US011253180B2

(12) United States Patent
Boukidjian et al.

(10) Patent No.: US 11,253,180 B2
(45) Date of Patent: Feb. 22, 2022

(54) METHODS AND APPARATUS FOR REDUCING CONTAMINATION IN BLOOD DRAW SAMPLES

(71) Applicant: DIGNITY HEALTH, San Francisco, CA (US)

(72) Inventors: Roy Boukidjian, Winnetka, CA (US); Gregoire Boukidjian, Winnetka, CA (US)

(73) Assignee: Dignity Health, San Francisco, CA (US)

( * ) Notice: Subject to any disclaimer, the term of this patent is extended or adjusted under 35 U.S.C. 154(b) by 495 days.

(21) Appl. No.: 16/085,849

(22) PCT Filed: Mar. 15, 2017

(86) PCT No.: PCT/US2017/022436
§ 371 (c)(1),
(2) Date: Sep. 17, 2018

(87) PCT Pub. No.: WO2017/160928
PCT Pub. Date: Sep. 21, 2017

(65) Prior Publication Data
US 2020/0297261 A1 Sep. 24, 2020

Related U.S. Application Data

(60) Provisional application No. 62/308,982, filed on Mar. 16, 2016.

(51) Int. Cl.
*A61B 5/15* (2006.01)
*A61B 5/154* (2006.01)

(52) U.S. Cl.
CPC ...... *A61B 5/150343* (2013.01); *A61B 5/1405* (2013.01); *A61B 5/15003* (2013.01); *A61B 5/154* (2013.01); *A61B 5/150351* (2013.01)

(58) Field of Classification Search
CPC ...... B65D 2571/00444; B65D 2571/00; B65D 21/0237–0238; B65D 21/10201;
(Continued)

(56) References Cited

U.S. PATENT DOCUMENTS 612,296 A 10/1898 Woodward
836,033 A 11/1906 Handy
(Continued)

FOREIGN PATENT DOCUMENTS

GB 2268804 A 1/1994

OTHER PUBLICATIONS

Binkhamis, K. et al. "Effect of the initial specimen diversion technique on blood culture contamination rates." Journal of clinical microbiology 52.3 (2014): 980-981.
(Continued)

*Primary Examiner* — Devin B Henson
*Assistant Examiner* — H. Q. Nguyen
(74) *Attorney, Agent, or Firm* — Quarles & Brady LLP

(57) ABSTRACT

Methods and apparatus are provided for increasing compliance with the discard volume method of blood drawing. The method includes attaching an initial discard container for discarding an initial amount of blood drawn to a standard blood culture bottle. The apparatus, detachable and configurable with a variety of standard blood culture containers, may act as a physical reminder and a convenient handling arrangement for drawing blood according to the preferred discard volume method that reduces sample contamination and false positives. These methods and apparatus may be compatible or retrofit with existing standard blood culture bottles or kits.

9 Claims, 10 Drawing Sheets

(58) Field of Classification Search
CPC ........ B65D 21/0201; B65D 71/50; A61J 1/05; A61J 1/14; B01L 3/502–5021; B01L 2200/141; A61B 5/153–1535; A61B 5/154; A61B 5/155; A61B 5/1405; A61B 5/150343; A61B 5/150351; Y10S 215/03; F16B 2/20; Y10T 24/3444

See application file for complete search history.

(56) References Cited

U.S. PATENT DOCUMENTS

| | | |
|---|---|---|
| 2,340,719 A | 2/1944 | Walter |
| 2,758,723 A | 8/1956 | Morris |
| 2,780,225 A | 2/1957 | Barr |
| 2,808,053 A | 10/1957 | Morris |
| 2,865,669 A | 12/1958 | Linthicum |
| 2,949,203 A | 8/1960 | Berg |
| 2,953,132 A | 9/1960 | Richter |
| 3,033,412 A | 5/1962 | Fox |
| 3,228,395 A | 1/1966 | Gewecke |
| 3,382,865 A | 5/1968 | Worrall, Jr. |
| 3,405,706 A | 10/1968 | Cinqualbre |
| 3,494,351 A | 10/1970 | Horn |
| 3,589,983 A | 6/1971 | Holderith |
| 3,604,410 A | 9/1971 | Whitacre |
| 3,730,170 A | 5/1973 | Michael |
| 3,817,240 A | 6/1974 | Tyres |
| 3,848,579 A | 11/1974 | Villa-Real |
| 3,848,581 A | 11/1974 | Cinqualbre |
| 3,890,203 A | 6/1975 | Mehl |
| 3,933,439 A | 1/1976 | McDonald |
| 3,939,822 A | 2/1976 | Markowitz |
| 3,985,135 A | 10/1976 | Carpenter |
| 4,036,387 A | 7/1977 | Feaster |
| 4,133,863 A | 1/1979 | Koenig |
| 4,150,089 A | 4/1979 | Linet |
| 4,154,229 A | 5/1979 | Nugent |
| 4,166,450 A | 9/1979 | Abramson |
| 4,192,919 A | 3/1980 | Raghavachari |
| 4,257,416 A | 3/1981 | Prager |
| 4,340,067 A | 7/1982 | Rattenborg |
| 4,370,987 A | 2/1983 | Bazell |
| 4,509,534 A | 4/1985 | Tassin, Jr. |
| 4,526,756 A | 7/1985 | Wong |
| 4,600,040 A | 7/1986 | Naslund |
| 4,676,256 A | 6/1987 | Golden |
| 4,703,761 A | 11/1987 | Rathbone |
| 4,856,647 A | 8/1989 | Dahne |
| 4,976,271 A | 12/1990 | Blair |
| 5,009,847 A | 4/1991 | Solomons |
| 5,084,034 A | 1/1992 | Zanotti |
| 5,097,842 A | 3/1992 | Bonn |
| 5,122,129 A | 6/1992 | Olson |
| 5,137,693 A | 8/1992 | Mawhirt |
| 5,269,317 A | 12/1993 | Bennett |
| 5,290,261 A | 3/1994 | Smith, Jr. |
| 5,330,464 A | 7/1994 | Mathias |
| 5,360,011 A | 11/1994 | McCallister |
| 5,375,726 A | 12/1994 | Lechleiter |
| 5,429,610 A | 7/1995 | Vaillancourt |
| 5,445,629 A | 8/1995 | Debrauwere |
| D363,211 S | 10/1995 | Noble |
| 5,456,887 A | 10/1995 | Calvo |
| 5,498,245 A | 3/1996 | Whisson |
| 5,505,721 A | 4/1996 | Leach |
| 5,507,299 A | 4/1996 | Roland |
| 5,555,920 A | 9/1996 | Godolphin |
| 5,620,008 A | 4/1997 | Shinar |
| 5,652,143 A | 7/1997 | Gombrich |
| 5,743,861 A | 4/1998 | Columbus |
| 5,762,633 A | 6/1998 | Whisson |
| 5,785,662 A | 7/1998 | Alexander |
| 5,871,699 A | 2/1999 | Ruggeri |
| 5,882,318 A | 3/1999 | Boyde |
| 6,016,712 A | 1/2000 | Warden |
| 6,159,164 A | 12/2000 | Neese |
| 6,210,909 B1 | 4/2001 | Guirguis |
| 6,287,265 B1 | 9/2001 | Gleason |
| 6,298,525 B1 | 10/2001 | Margo |
| 6,364,890 B1 | 4/2002 | Lum |
| 6,387,086 B2 | 5/2002 | Mathias |
| 6,506,165 B1 | 1/2003 | Sweeney |
| 6,543,100 B1 | 4/2003 | Finley |
| 6,565,054 B2 | 5/2003 | Weesner |
| 6,626,884 B1 | 9/2003 | Dillon |
| 6,692,479 B2 | 2/2004 | Kraus |
| 6,746,420 B1 | 6/2004 | Prestidge |
| 6,843,775 B2 | 1/2005 | Hyun |
| 6,913,580 B2 | 7/2005 | Stone |
| 7,044,941 B2 | 5/2006 | Mathias |
| 7,087,047 B2 | 8/2006 | Kraus |
| 7,335,188 B2 | 2/2008 | Graf |
| 8,034,033 B2 | 10/2011 | Grinberg |
| 8,047,589 B1 | 11/2011 | Trainor |
| 8,197,420 B2 | 6/2012 | Patton |
| 8,197,771 B2 | 6/2012 | Maiden |
| 8,221,360 B2 | 7/2012 | Fletcher |
| 8,231,546 B2 | 7/2012 | Patton |
| 8,337,418 B2 | 12/2012 | Patton |
| 8,535,241 B2 | 9/2013 | Bullington |
| 8,647,286 B2 | 2/2014 | Patton |
| 8,684,433 B2 | 4/2014 | Oesterle |
| 8,864,684 B2 | 10/2014 | Bullington |
| 8,876,734 B2 | 11/2014 | Patton |
| 9,022,950 B2 | 5/2015 | Bullington |
| 9,022,951 B2 | 5/2015 | Bullington |
| D731,643 S | 6/2015 | Bullington |
| 9,060,724 B2 | 6/2015 | Bullington |
| 9,060,725 B2 | 6/2015 | Bullington |
| 9,149,576 B2 | 10/2015 | Bullington |
| 9,155,495 B2 | 10/2015 | Bullington |
| 9,204,864 B2 | 12/2015 | Bullington |
| 2003/0061690 A1* | 4/2003 | Finley .................. F16B 2/20 24/336 |
| 2004/0127816 A1 | 7/2004 | Galvao |
| 2005/0281713 A1 | 12/2005 | Hampsch |
| 2006/0129064 A1 | 6/2006 | Conway |
| 2006/0287639 A1 | 12/2006 | Sharp |
| 2007/0176071 A1 | 8/2007 | Borchardt |
| 2009/0254030 A1 | 10/2009 | Sarraf |
| 2011/0198361 A1 | 8/2011 | Chen |
| 2014/0155782 A1 | 6/2014 | Bullington |
| 2014/0276578 A1 | 9/2014 | Bullington |
| 2015/0014492 A1 | 1/2015 | Sharpe |
| 2015/0032067 A1 | 1/2015 | Bullington |
| 2015/0073348 A1 | 3/2015 | Bullington |
| 2015/0094615 A1 | 4/2015 | Patton |
| 2015/0246352 A1 | 9/2015 | Bullington |
| 2015/0250414 A1 | 9/2015 | Bullington |
| 2015/0257691 A1 | 9/2015 | Bullington |
| 2015/0342510 A1 | 12/2015 | Bullington |
| 2015/0351678 A1 | 12/2015 | Bullington |
| 2015/0351679 A1 | 12/2015 | Bullington |
| 2015/0367069 A1 | 12/2015 | Bullington |

OTHER PUBLICATIONS

Garcia, R. A., et al. "Multidisciplinary team review of best practices for collection and handling of blood cultures to determine effective interventions for increasing the yield of true-positive bacteremias, reducing contamination, and eliminating false-positive central line-associated bloodstream infections." American journal of infection control 43.11 (2015): 1222-1237.

Patton, RG et al. "Innovation for reducing blood culture contamination: initial specimen diversion technique" Journal of clinical microbiology 48.12 (2010): 4501-4503.

European Patent Office. Extended European Search Report for application 17767397.7 dated Aug. 19, 2019.

(56) References Cited

OTHER PUBLICATIONS

International Searching Authority. International Search Report and Written Opinion for application PCT/US2017/022436, dated Jun. 8, 2017.

* cited by examiner

METHODS AND APPARATUS FOR REDUCING CONTAMINATION IN BLOOD DRAW SAMPLES

CROSS-REFERENCE TO RELATED APPLICATIONS

This application represents the U.S. National Stage of International Application No. PCT/US2017/022436 filed Mar. 15, 2017 which is based on, claims priority to, and incorporates herein by reference U.S. Provisional Application Ser. No. 62/308,982, filed Mar. 16, 2016, and entitled, "METHODS AND APPARATUS FOR REDUCING CONTAMINATION IN BLOOD DRAW SAMPLES."

STATEMENT REGARDING FEDERALLY SPONSORED RESEARCH

N/A

BACKGROUND

Blood tests are one of the most common medical diagnostic tools used in the world today. One particular type of blood test is a blood culture. Blood cultures are ordered to detect the presence of bacteria, fungi, and other microorganisms in patients' blood, to monitor antimicrobial therapy, and to identify a blood infection or septicemia. At just one hospital, there may be about 34,000 blood cultures ordered and drawn per year. The results of these tests are used to guide healthcare professionals in determining the best course of treatment to recommend for their patients. Blood cultures are relevant to life-threatening infections such as bacteremia and fungemia, as well as focal infections, osteomyelitis, meningitis, and infective endocarditis. These diagnoses and treatment decisions may incur significant costs for everyone involved, including for example, prolonged hospital stays or use of antibiotics.

Blood cultures may be contaminated by pathogens external to patients and return false positives. When a blood culture returns a false positive, wrong conclusions may be drawn and continue in a cascade of errors, all stemming from the initial misinformation. Not only can false positives lead to unnecessary treatments, but they can also cause delay in badly needed proper diagnosis and care or even adverse patient events, including the introduction of pathogens which actually develop new blood infections. False positives cost millions of dollars annually in unnecessary healthcare procedures and treatments. Additionally, the time costs and untold burdens on the patients and those around them associated with false positives are far too excessive.

The College of American Pathologists reports that rates of blood culture contamination can range up to 6% in participating hospitals. The Clinical Microbiology Laboratories has set the benchmark rate for contamination at less than 3%. The estimated additional health care costs per contaminated blood culture range from $1,000 to $10,000.

One of the common sources for sample contamination is the skin of the patients themselves, which is exposed to and protects their internal systems from all manner of bacteria and other microorganisms. When drawing blood from a subject, the hollow needle first punctures the skin before reaching the vein to be tapped. This initial poke can introduce any of those previously mentioned external contaminants into the body and subsequently into the blood culture container. After introduction into the sample, the laboratory running the test may be unable to tell if any bacteria or fungi found were not actually representative of the subject's internal system. Thus, impurities common to the skin are reported out as indicating a more serious affliction within a patient.

Efforts to prevent this type of blood culture contamination have included thoroughly cleansing the skin at the site before piercing with the needle, avoiding taking samples from IV lines and using venipuncture instead, and phlebotomists using sterile equipment and gloves. For example, innovations within these solutions have included new applicator devices for the aseptic preparation of the puncture site with chlorhexidine.

Another way to prevent this type of blood culture contamination has emerged called the Discard Volume Method (DVM) for obtaining blood samples from patients. In the DVM, after the initial puncture of the skin, a small volume of blood is drawn and then discarded along with any foreign matter it happened to contain. The unadulterated blood sample is then collected and saved for analysis. Recent studies have shown that using the DVM may cut down false positives from blood culture contamination by about 30%, saving up to an estimated $1.2 million.

However, while the DVM shows promising results, it has not been widely implemented. Without intending to be bound by theory, this lack of DVM usage may be due to the inherent waste the method itself creates in discarding the initial volume of blood drawn. Healthcare practitioners may perceive the DVM as a waste of time and money. In particular, practitioners may not remember to grab extra sample vials or kits for one blood culture out of habit. Also, blood culture bottles or kits cost from $2 up to $30 each due to their special coating agents, broths, and vacuum preparations. Thus, it is further instinctive not to discard one of these expensive blood culture bottles.

Therefore, in the face of these resistant forces, it would be desirable to have methods and apparatus for ensuring compliance with the DVM, thereby reducing the number of false positives from blood culture contamination.

SUMMARY

The present disclosure provides methods and apparatus for reducing the occurrence of blood test false positives by controlling against blood culture contamination. In accordance with the present disclosure, systems and methods are provided to improve compliance with the discard volume method (DVM) by providing a container specifically for collecting the initial discard volume of blood from the patient. The addition of a container provided in a readily-accessible way to receive the initial blood drawn and be discarded serves as both a physical reminder and a convenient way to handle the implements needed to carry out the preferred method of drawing blood for the phlebotomist or other healthcare provider.

In accordance with one aspect of the disclosure, an apparatus for use with a blood culture bottle and for enhancing compliance with the discard volume method for drawing blood from a patient is provided. The apparatus includes an initial discard container with a body having an opening and an inner volume sized to contain an initial amount of blood drawn from the patient. The initial discard container also includes a cap configured to cover the opening and seal the inner volume. The apparatus further includes a connector configured to connect the initial discard container to the blood culture bottle.

In accordance with another aspect of the disclosure, a system for reducing blood culture contamination when drawing blood from a patient is provided. The system includes an initial discard container sized to contain an initial amount of blood drawn from the patient and a blood culture bottle configured to contain subsequent blood drawn from the patient to be tested. The initial discard container is detachably connected to the blood culture bottle.

In accordance with yet another aspect of the disclosure, a method for reducing blood culture contamination is provided. The method includes drawing an initial amount of blood from a patient and placing the initial amount of blood into an initial discard container configured to be coupled to a blood culture bottle with a connector. The method also includes drawing blood to be tested from the patient and placing the blood to be tested into the blood culture bottle.

DETAILED DESCRIPTION

The discard volume method (DVM) can drastically reduce blood sample contamination caused by an initial needle puncture introducing foreign matter from the skin into the blood stream. In particular, the DVM includes taking a small volume of blood collected after the initial needle puncture of the skin and discarding it. The actual blood sample is then drawn and saved for laboratory testing. By making the DVM easier, more accessible, and less costly, more healthcare professionals will implement it, thereby lowering the rate of false positives caused by contamination and saving millions in unnecessary healthcare costs annually.

The present disclosure provides methods and apparatus for enhancing the convenience and lowering the cost of compliance with the DVM of drawing blood. As discarding the initial volume of blood is key to the DVM, the present disclosure provides an apparatus comprising a container especially for that purpose, thus making the DVM easier to use. The present disclosure seeks to avoid utilizing complex mechanical switching mechanisms to implement the DVM since these systems are not only expensive, but more susceptible to failure because of multiple complications that could break at any time. Further, the present disclosure includes an initial discard container compatible for inclusion with various existing standard blood culture bottles, in some applications with a modular connection. Thus, the initial discard container of the present disclosure provides an improvement over prior systems and may be retrofit to work well with many existing systems used in healthcare facilities.

Figure 1:
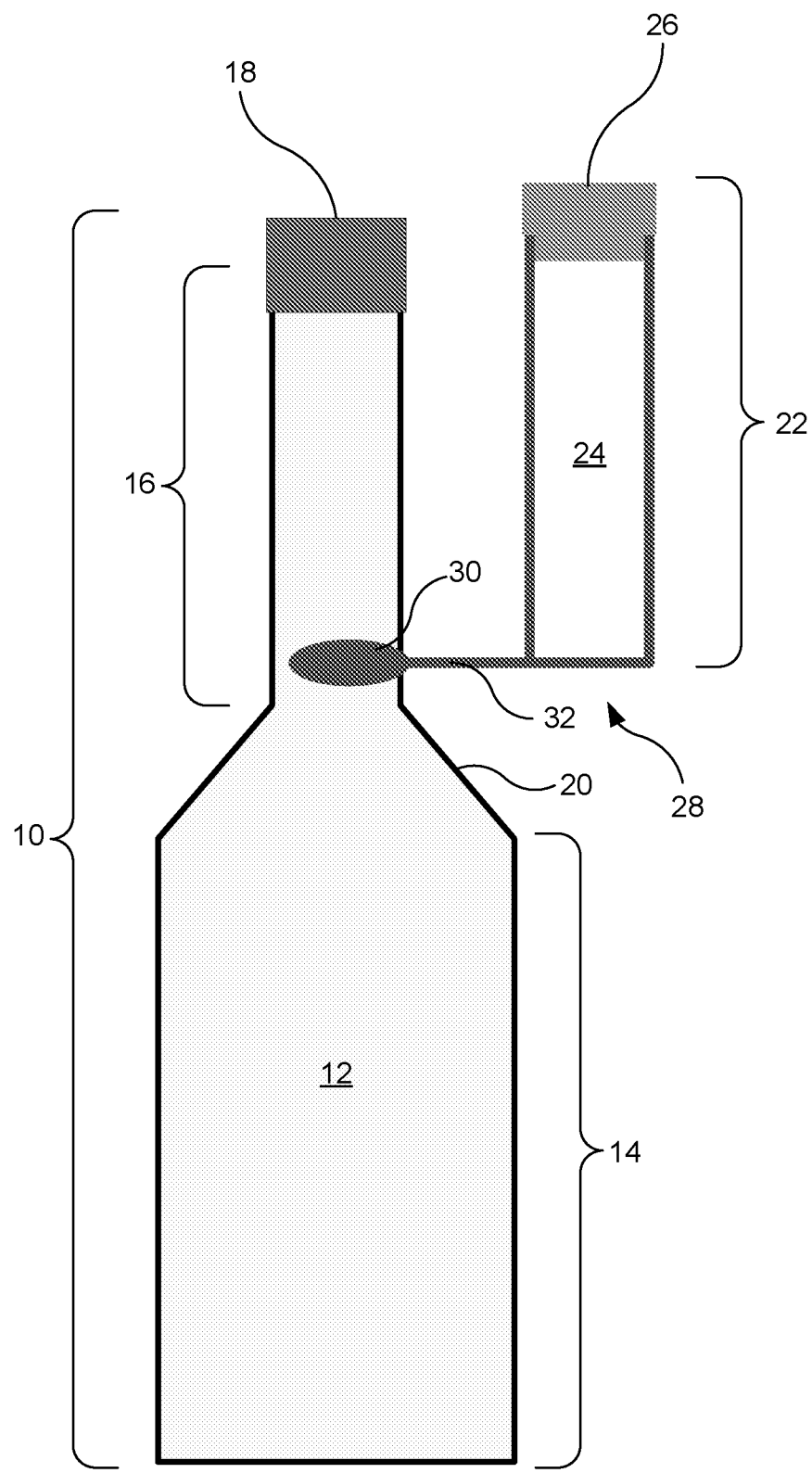
FIG. 1 shows a side view of an example configuration of a standard blood culture bottle with an initial discard container attached via a connector in accordance with the present disclosure.
Figure 2:
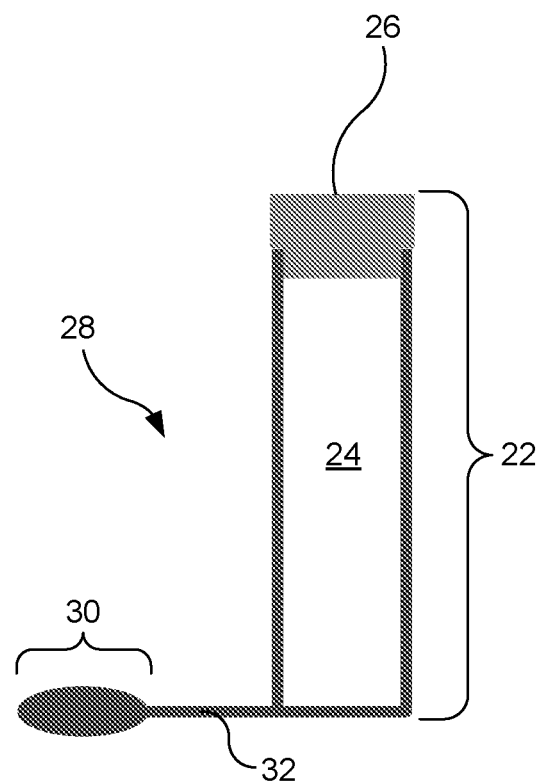
FIG. 2 shows a side view of the initial discard container and the connector of FIG. 1.

In a typical blood culture procedure, a blood sample is collected from one venipuncture and then inoculated into one or more blood culture bottles. An example culture bottle 10 is shown in FIG. 1, including an inner volume 12 for holding, for example, 10 ml of blood. Generally, standard blood cultures are ordered as a set so that assembled collection equipment requires both an aerobic bottle 10 and an anaerobic bottle 10. Thus, standard blood culture bottles or containers 10 are packaged in pairs and include special nutritionally enriched broths, agar media, coatings, or resins for helping grow bacteria or fungi present in the cultures.

These standard blood culture bottles 10 are sized for particular trays or stacks within computerized detection instrumentation systems and laboratory equipment designed by the same manufacturer. These highly organized systems streamline laboratory processes and incorporate verification steps for reducing errors in results. The FDA classifies blood culture bottles as in vitro diagnostic devices, and they are defined under regulation 21 C.F.R. § 866.2860 as part of a microbial growth monitor system. Other equipment and devices used in the blood drawing procedure of a blood culture test are defined under 21 C.F.R. § 862.1675 as class II tubes, vials, and other devices for blood-specimen collection. Market regulations and the use of automated laboratory systems have resulted in standardized dimensions for any commercially available blood culture bottles and containers. Table 1 contains details of the most popular manufacturers' standard blood culture bottles.

TABLE 1

| Manufacturer | Bottle | Volume | Cost |
|---|---|---|---|
| Becton, Dickinson, & Co. | BACTEC | 40 mL | $10.77 |
| Becton, Dickinson, & Co. | SEPTI-CHEK | 70 mL | $2.00 |
| bioMerieux | BacT/Alert | 40 mL | $6.16 |
| Thermo Scientific VersaTREK | REDOX | 80 mL | $5.50 |
| Thermo Scientific VersaTREK | REDOX EZ Draw | 40 mL | $5.80 |

As shown in FIG. 1, the blood culture bottle 10 includes a base 14, a neck 16, and a lid 18. Both the base 14 and the neck 16 may be substantially cylindrical and uniform. The base 14 makes up the lower half of the blood culture bottle 10, which then tapers quickly at a taper portion 20 to the narrower neck 16 at an angle between 30° and 80° with respect to the vertical wall of the base 14. For example, the Becton, Dickinson, & Co. BACTEC blood culture bottle is about 5" tall with a 0.55" diameter neck 16 that is about 2" long.

The neck 16 of the blood culture bottle 10 includes an opening at the top which may be sealed by the lid 18. The lid 18 may fit inside the opening of the neck 16 or around the neck 16, such as in a screw-type fitting, for example. The lid 18 may be color coded to represent the anaerobic or aerobic type or to identify the type of culture media within the bottle 10. In an alternate configuration, such as a bioMerieux BacT/Alert bottle, the base 14 of the blood culture bottle 10 may extend to the lid 18 or have a relatively short neck 16 (that is, the blood culture bottle 10 may not include a taper portion 20, or include a very short taper portion 20).

Current ways of implementing the DVM include using a blood culture bottle 10, such as that shown in FIG. 1. In particular, an initial volume of blood drawn is disposed into the culture bottle 10, and then the culture bottle 10 is discarded. Additional blood is then drawn for testing and disposed into additional culture bottle(s) 10. Thus, current methods generally require three or more blood culture bottles 10: one for the initial blood drawn to be discarded and two or more for the later blood drawn to be tested (e.g., at least an aerobic bottle 10 and an anaerobic bottle 10). As bottles 10 are packaged in pairs, practitioners may not remember to grab extra sample bottles 10 or kits for a single blood culture out of habit. Also, as shown in Table 1 above, blood culture bottles 10 or kits can be costly due to their special coating agents, broths, and vacuum preparations. Thus, it is further instinctive not to use one of these expensive blood culture bottles 10 for a small volume of blood that is to be discarded.

In one aspect, the present disclosure provides an apparatus for enhancing compliance with the DVM. As shown in FIG. 1, the apparatus may be a discard volume tube, via, or initial discard container 22 for holding the initial volume of blood drawn to be discarded when using the DVM. The initial discard container 22 may make it more convenient to implement the DVM because of its ergonomic design. For example, the initial discard container 22 may be configured to be easily held in a practitioner's hand or easily attached to a blood culture bottle 10, as further described below. In some aspects, as shown in FIG. 1, the initial discard container 22 may be a generally uniform cylindrical tube. Alternatively, the initial discard container 22 may be any shape, for example spherical.

According to one study of blood culture contamination rates, discarding an initial volume of about 5 ml was effective in lowering false positives by about 30%, versus initial discard volumes of 1-2 ml. In order to meet this metric and in light of ergonomics, a preferred configuration for the initial discard container 22 may be smaller than the standard blood culture bottle 10 and include an inner volume 24 capable of holding about 6.6 ml. Alternatively, the initial discard container 22 may be any other volume within the inner volume 24 above 5 ml, such as between about 5 ml and about 10 ml. Other volumes below 5 ml may also be contemplated.

Figure 10:
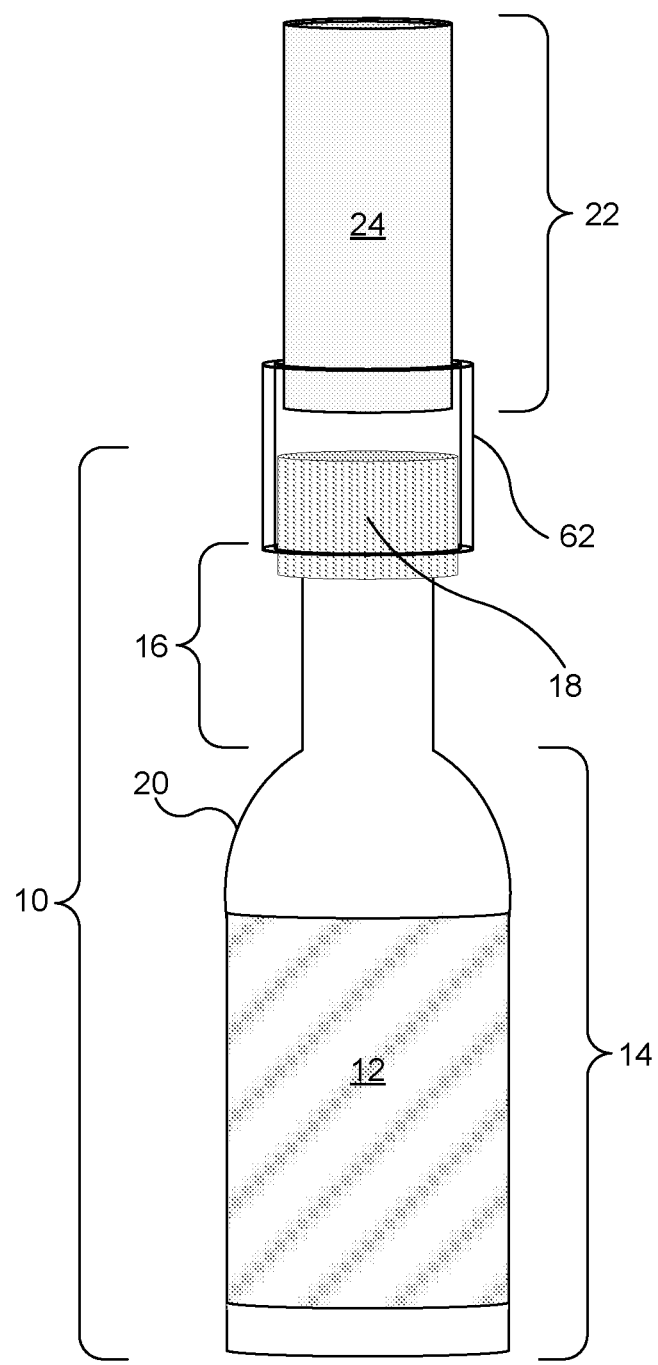
FIG. 10 shows a perspective view of yet another example configuration of a standard blood culture bottle with an initial discard container attached via a connector in accordance with the present disclosure.

The initial discard container 22 may include a cap 26 (or stopper or lid) for sealing the inner volume 24 to prevent blood from leaking. The cap 26 may act as a seal for a vacuum created within the inner volume 24 of the initial discard container 22. The cap 26 may be made of rubber or other material so that a needle may be pushed through the cap 26 to initiate blood flow from the patients' vein into the inner volume 24. The cap 26 may be coated with sterilizing material or a lubricant such as silicone. The cap 26 may be integrally connected to the initial discard container 22 or otherwise attached to keep the two components together. Furthermore, the initial discard container 22 may include additional caps 26. Alternatively, the initial discard container 22 may not include a cap 26 (such as shown in FIG. 10). For example, the initial discard container 22 may be configured such that twisting or other manipulation of a top end of the initial discard container 22 seals the initial amount of blood drawn inside the inner volume 24.

In some aspects, the initial discard container 22 may be formed of an inexpensive plastic or other material. The initial discard container 22 may also be sterilized or evacuated during manufacture. In addition or alternatively, the initial discard container 22 may be sterilized prior to use or may include wipes or other components to conveniently sterilize the device or puncture site prior to blood draw. The initial discard container 22 (and/or a comprehensive kit, as further described below) may sustain a long shelf life within healthcare facilities, which may be helpful in managing stock or purchasing in bulk.

Advantageously, the initial discard container 22 need not include any special substances, such as those in the inner volume 12 of blood culture bottles 10, since the initial blood volume drawn may simply be discarded along with the initial discard container 22. Alternatively, the inner volume 24 of the initial discard container 22 may be coated with a special compound and/or include other broths in order to prevent growth or keep the initial discard container 22 sterile. In this respect, the initial discard container 22 may be kept rather than discarded in order to test the success rate of the DVM in reducing false positives from the initial blood drawn. Also, the initial discard container 22 may include a special formula or other compound that may provide the phlebotomist with an initial visual cue about the contents of the blood. In this way, the initial discard container 22 may act as a diagnostic device.

In some aspects, the initial discard container 22 may be included in a kit with, for example, two blood culture bottles 10, sterile needles, and/or other equipment. Additionally, the initial discard container 22 may be attachable to and/or detachable from a component of the kit or another commonly used implement in obtaining a blood culture, such as a culture bottle 10, syringe, tubing, or tray. For example, as further described below, the initial discard container 22 may be attachable to and/or detachable from one or both of the blood culture bottles 10 via a snap-off, a tear-off, a lift-off, or another connection.

Figure 5:
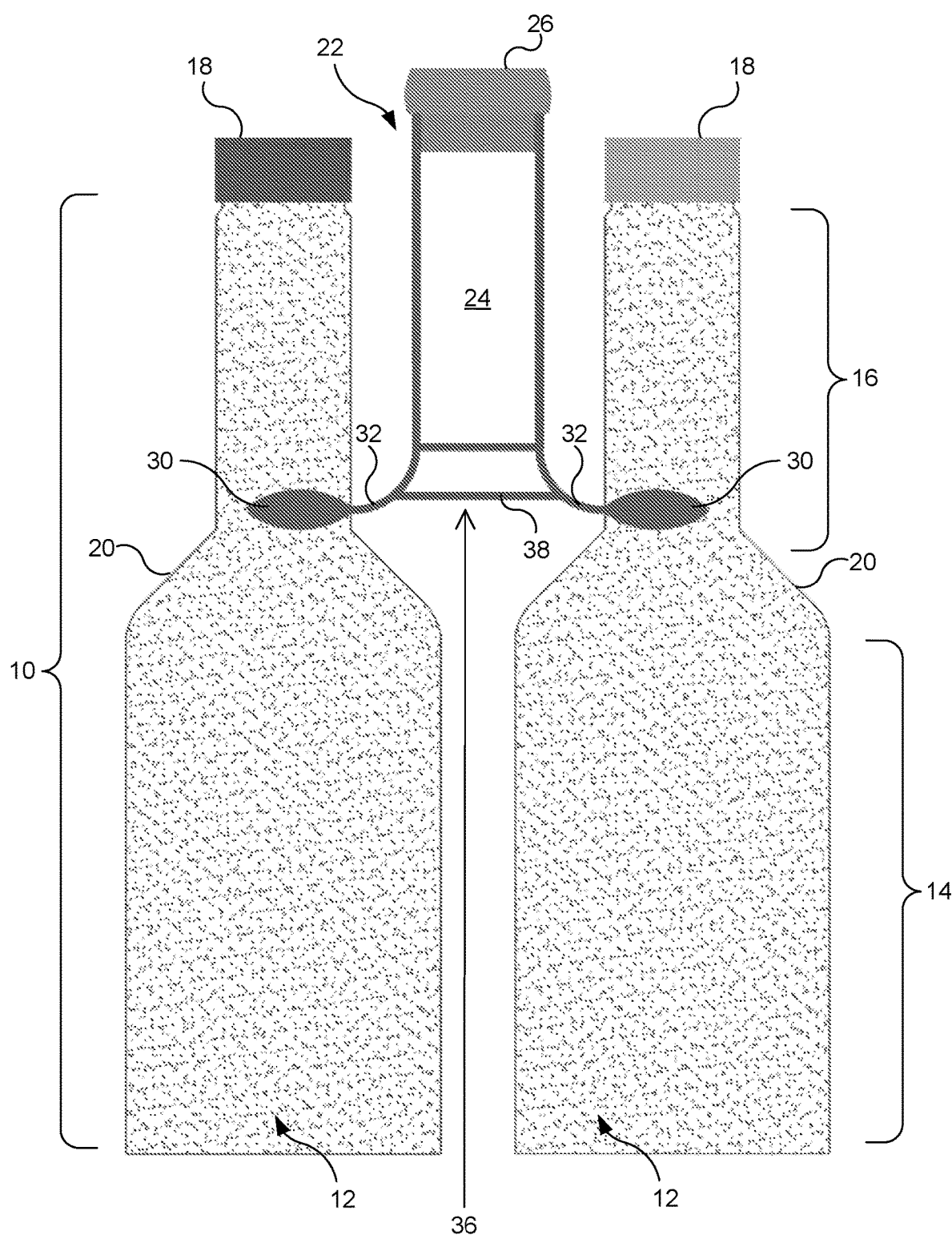
FIG. 5 shows a side view of another example configuration of an initial discard container and a connector in accordance with the present disclosure.
Figure 6:
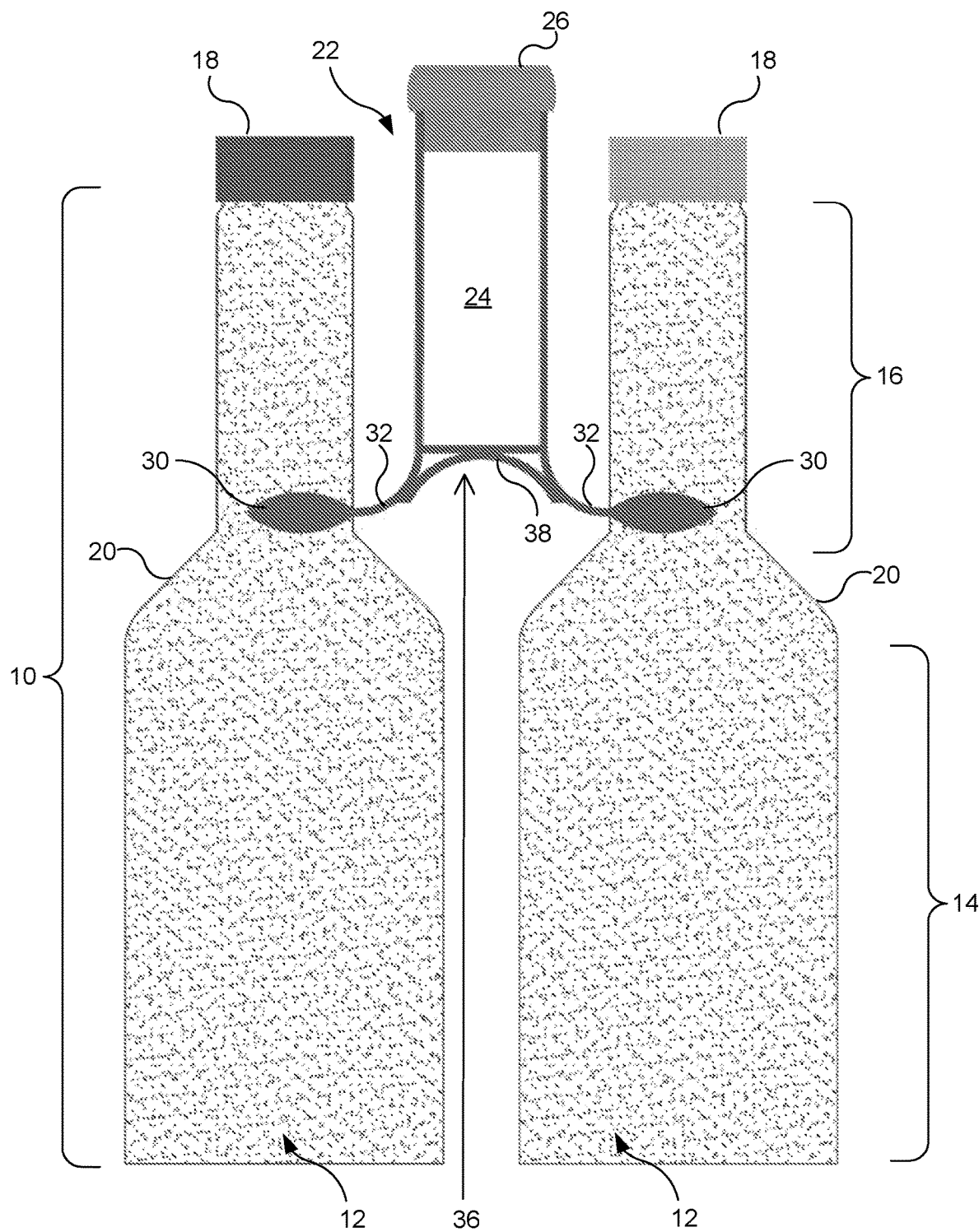
FIG. 6 shows a side view of another example configuration of the initial discard container and the connector of FIG. 5.
Figure 7:
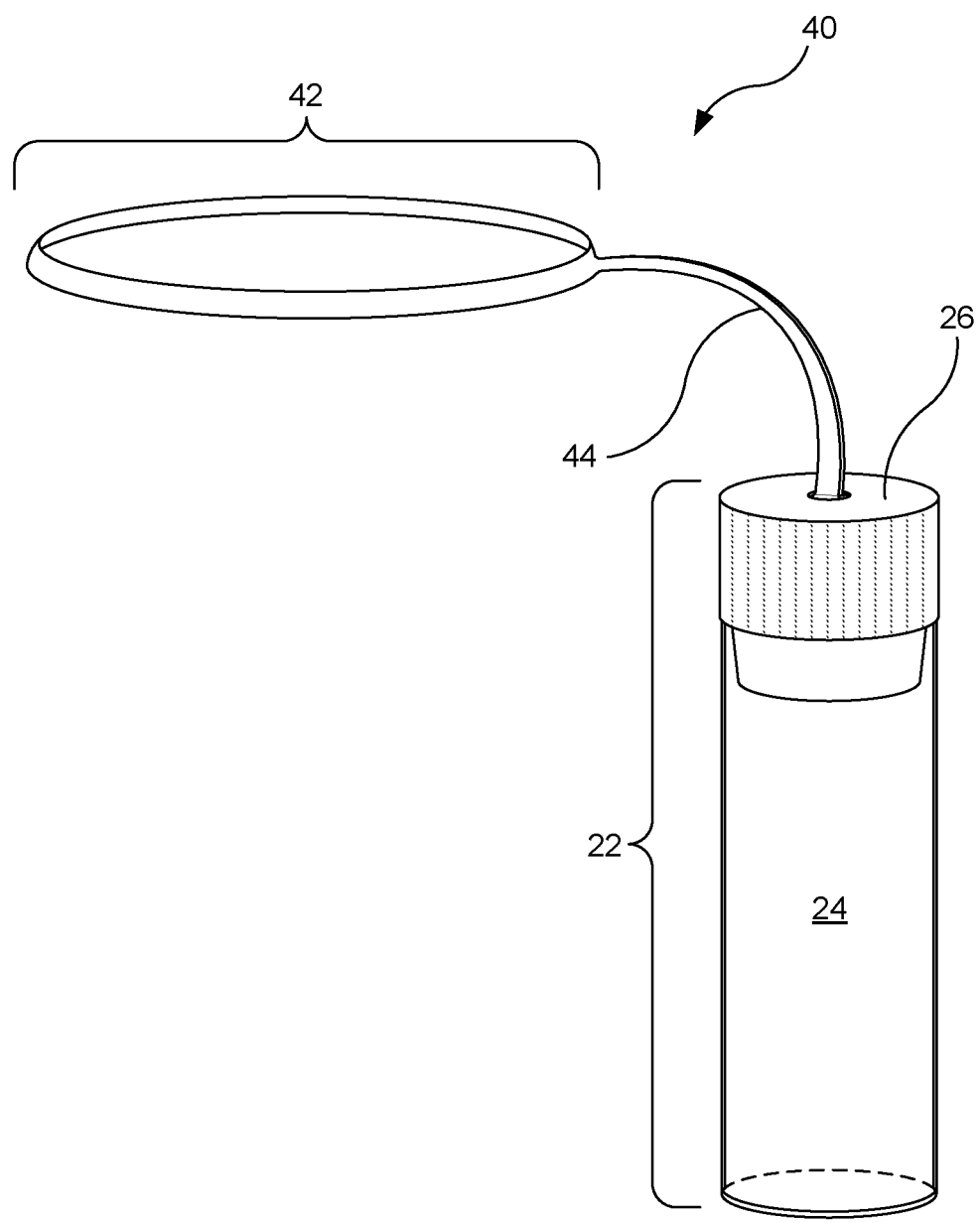
FIG. 7 shows a perspective view of yet another example configuration of an initial discard container and a connector in accordance with the present disclosure.
Figure 8:
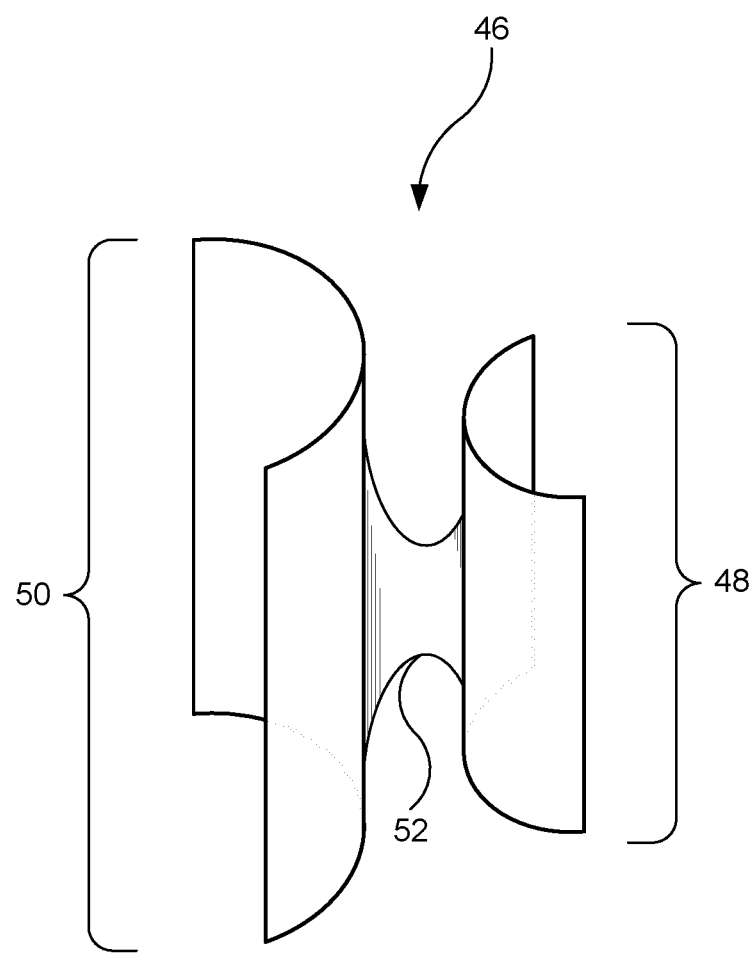
FIG. 8 shows a perspective view of yet another example configuration of an initial discard container and a connector in accordance with the present disclosure.
Figure 9:
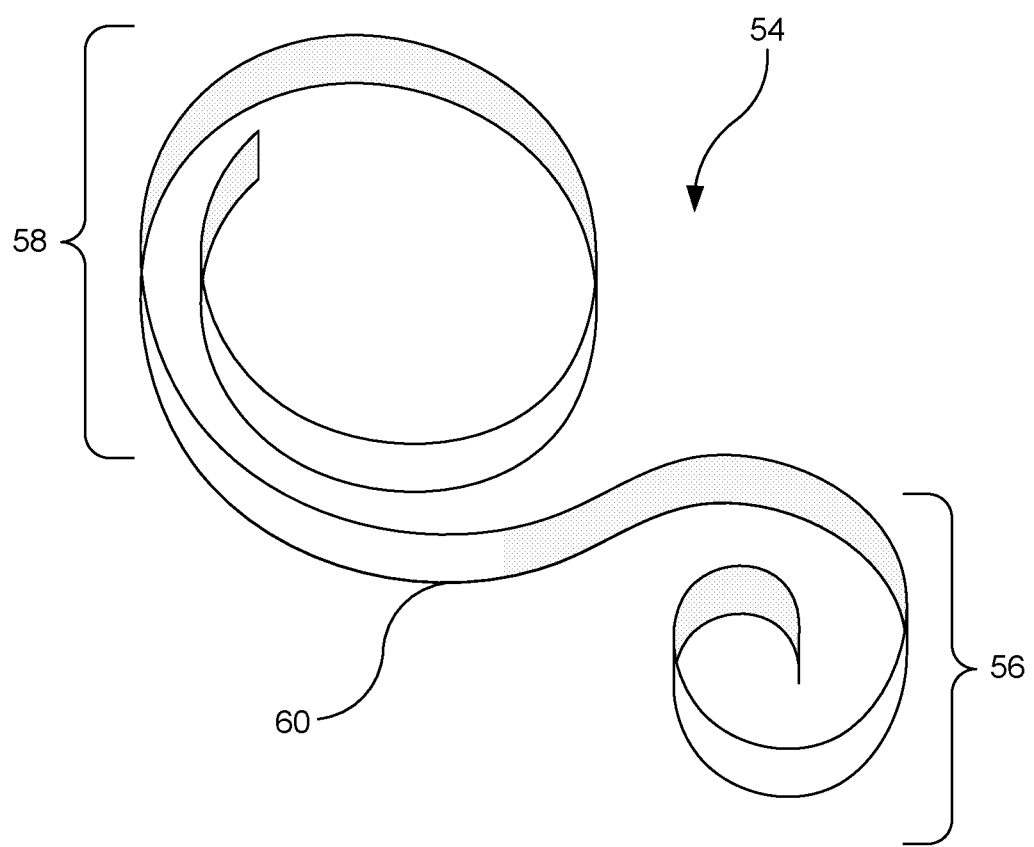
FIG. 9 shows a perspective view of yet another example configuration of an initial discard container and a connector in accordance with the present disclosure.

In one configuration, an initial discard container 22 may be removably coupled to a blood culture bottle 10. In one non-limiting example, as shown in FIGS. 1-4, a connector 28 may provide this attachable and/or detachable functionality as a clip integral with the initial discard container 22 and configured to be removably coupled to a culture bottle 10. In another example, as shown in FIGS. 5-6, a connector 36 may act as a clip integral with or capable of holding the initial discard container 22 and configured to be removeably coupled to both blood culture bottles 10. In another configuration, the initial discard container 22 may be formed as an extension of or extending from the lid 18 of one of the blood culture bottles 10. In this non-limiting example, as the equipment is prepared for the blood draw, the phlebotomist may snap-off or tear-off the initial discard container 22 from the lid 18 before use. Alternatively, as shown in FIG. 7, a connector 40 may be integral with a cap 26 of an initial discard container 22 and attachable to a blood culture bottle 10. In yet other configurations, as shown in FIGS. 8-10, a connector 46, 54, 62 may be completely separate from the initial discard container 22. In such configurations, the connectors may be attachable to and detachable from both the initial discard container 22 and the blood culture bottle(s) 10. Further, a standard blood collection tube may operate as the initial discard container 22.

Figure 3:
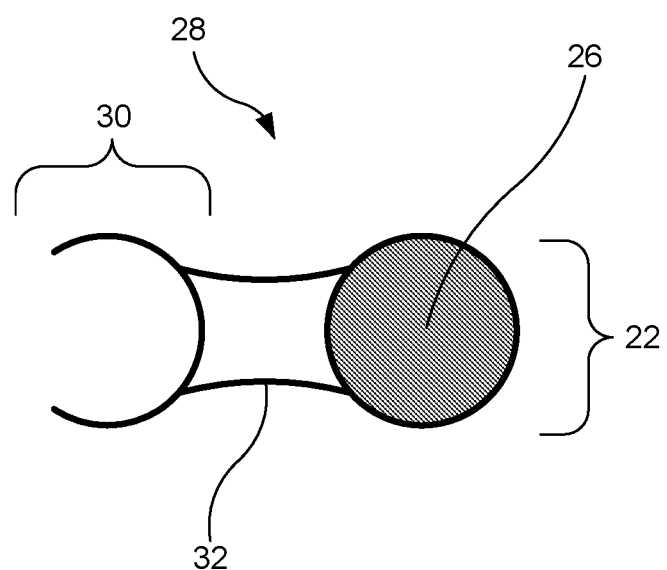
FIG. 3 shows a top view of the initial discard container and the connector of FIG. 1.

Referring to the example of FIGS. 1-4, a connector 28 may releasably couple the initial discard container 22 to a blood culture bottle 10. More specifically, the connector 28 may include an integral initial discard container 22, an attachment mechanism 30, and an intermediate portion 32 positioned between the attachment mechanism 30 and the initial discard container 22. As such, the attachment mechanism 30 may be integrally connected to a body portion of the initial discard container 22 via the intermediate portion 32. The attachment mechanism 30 can be sized to releasably attach to a blood culture bottle 10. For example, as shown in FIG. 3, the attachment mechanism 30 may be a compression-fit clip configured to snap or clip onto a side of a blood culture bottle 10 (thus providing a snap-off or tear-off connection). An attachment site for the attachment mechanism 30 may be at the neck 16 and/or base 14 of the bottle 10, as shown in FIG. 1. In some configurations, the connector 28 may be elongated so that the attachment mechanism 30 clamps around about half of the cylinder shaped portion of the neck 16 or the base 14 of a blood culture bottle 10. In other configurations, the attachment mechanism 30 may be longer to fit around between one half the circumference and the entire circumference of the neck 14 or the base 16. Additionally, in some configurations, the connector 28 and, more specifically, the attachment mechanism 30, may be sized and configured so that it is flexible enough to attach to a variety of sizes of blood culture bottles 10.

Figure 4:
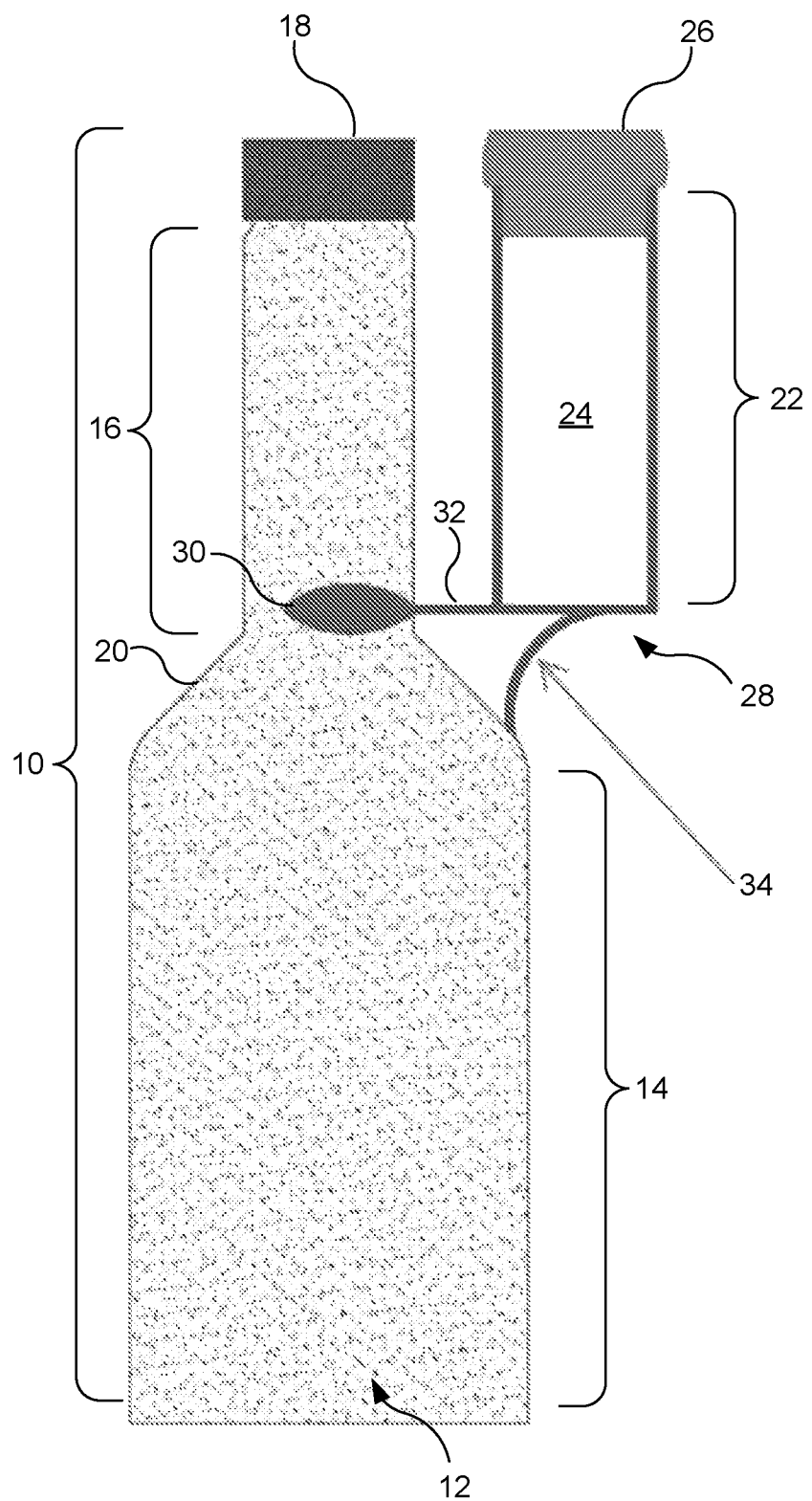
FIG. 4 shows a side view of another example configuration of the initial discard container and the connector of FIG. 1.

Additionally, in some configurations, as shown in FIG. 4, the connector 28 may include a support member 34. The support member 34 may help support and stabilize the connector 28 against the blood culture bottle 10 and/or may serve as a finger rest for a practitioner carrying the blood culture bottle/discard container combination.

Referring now the examples of FIGS. 5-6, a connector 36 may be similar to connector 28, but configured to attach to a set of two blood culture bottles 10. As such, the connector 36 may include an integral initial discard container 22, two attachment mechanisms 30, and two intermediate portions 32 separating each respective attachment mechanism 30 from the initial discard container 22. Additionally, the connector 36 may include a support bar 38 connecting the two intermediate portions 32. The support bar 38 can help support and stabilize the connector 36 against the blood culture bottles 10. The support bar 38 may be substantially horizontal, as shown in FIG. 5, or may be curved upward and serve as a finger rest for a practitioner carrying the blood culture bottles/discard container combination, as shown in FIG. 6.

While the above examples describe and illustrate connectors 28, 36 integral with the initial discard container 22, it is contemplated within other configurations to have such connectors 28, 36 be separate from the initial discard container 22. For example, the initial discard container 22 may be held in, received in, or otherwise attached to the connectors 28, 36.

Referring to the example of FIG. 7, a connector 40 may include a hook or loop 42 configured to couple an initial discard container 22 to a blood culture bottle 10, thus providing a lift-off connection. The loop 42 may extend from a cap 26 of the initial discard container 22. In other words, the loop 42 may be connected to or integral with the cap 26 via an intermediate portion 44. Also, the loop 42 may be sized to fit around, for example, the blood culture bottle neck 16, but not the base 14. Thus, the loop 42 hangs the initial discard container 22 around the neck 16 of the blood culture bottle 10 and rests against an upper portion of the base 14 (such as along the taper portion 20) for convenience. These looped initial discard containers 22 may be easily added to blood culture bottles 10 lined up in a storage closet.

Additionally, in some configurations, the loop 42 may be configured so that it can be tightened or synched. As a result, the loop 42 can tighten or synch around, for example, the neck 16 of a blood culture bottle 10, thus providing a secure and robust connection between the initial discard container 22 and the blood culture bottle 10.

Referring to the example of FIG. 8, a connector 46 may be a separate mechanism that releasably couples the initial discard container 22 to a blood culture bottle 10. More specifically, the connector 46 may include a discard container attachment mechanism 48 that is sized to releasably attach to or clip on the initial discard container 22, and a bottle attachment mechanism 50 that is sized to releasable attach to or clip on a blood culture bottle 10. The attachment mechanisms 48, 50 may be coupled together by an intermediate portion 52. Similar to the attachment mechanism 30 of FIGS. 1-4, the attachment mechanisms 48, 50 may be compression-fit clips configured to snap or clip onto a side of the initial discard container 22 and the blood culture bottle 10, respectively. Also, like the attachment mechanism 30 of FIGS. 1-4, the attachment mechanism 50 may be sized and configured to attach around the neck 16 or the base 14 of a blood culture bottle 10. The attachment mechanisms 48, 50 may each have a length sized to fit around between about one half to one whole of a circumference of the initial discard container 22 and the blood culture bottle 10, respectively.

Referring to the example of FIG. 9, a connector 54 may be a separate mechanism that releasably couples the initial discard container 22 to a blood culture bottle 10. More specifically, the connector 54 may include a discard container attachment mechanism 56 that is sized to releasably attach to the initial discard container 22 and a bottle attachment mechanism 58 that is sized to releasably attach to the blood culture bottle 10. The attachment mechanisms 56, 58 may include loop-type configurations that operate in a similar fashion to the loop 42 of FIG. 7 and may be connected by an intermediate portion 60. In some configurations, the connector 54 may allow for more flexible connection to a greater variety of blood culture bottles 10. That is, the connector 54 may include a flexible loop attachment mechanism 58 that can shrink or expand to attach to a neck 16 or a base 14 of different-sized blood culture bottles 10. For example, the connector 54 may comprise a moldable material or be a coated wire that facilitates various tensions and orientations of the connector 54 and attached initial discard container 22 relative to the blood culture bottle 10. In such a configuration, the connector 54 may be a single integral piece. However, in other configurations, the connector 54 may comprise two or more pieces coupled together.

Referring to the example of FIG. 10, a detachable connecter 62 for attachment of an initial discard container 22 to a blood culture bottle 10 may be provided as a sleeve-type connector that connects the initial discard container 22 to a lid 18 of the blood culture bottle 10. For example, the connector 62 may be shaped like a hollow uniform tube. The connector 62 may be flexible plastic, rubber, or silicone that fits snugly around at least a portion of the body of the initial discard container 22 and an upper end of the lid 18 of the blood culture bottle 10. Alternatively, the connector 62 may fit over the entire lid 18 and/or may be integral with the initial discard container 22. In either configuration, the connector 62 may provide a lift-off type connection (that is, a practitioner can disconnect the connector 62 from the blood culture bottle 10 by lifting the connector 62 or the initial discard container 22 off the bottle cap 18). In one configuration, the connector 62 may be sized and configured so that it is compatible with a standard blood collection tube with approximate dimensions of 0.5"×4", such as a Becton Dickinson Vacutainer® tube. Additionally, in some configurations, the connector 62 may be a one-time-use detachable connection between the initial discard container 22 and the blood culture bottle 10, such as a shrink wrap or adhesive tape that may be torn off (thus facilitating a tear-off connection). In such configurations, the connector 62 may save shelf or package space by creating a smaller footprint than connectors which position the two containers side-by-side. Moreover, a neck-to-container continuous connection facilitated by the connector 62 (that is, from the bottle neck 16 to the initial discard container 22) may be more ergonomic and easier to grab.

The connectors of FIGS. 1-10 and the initial discard container 22 may be sold together and/or individually. For example, the connectors and the initial discard container 22 may be attached to blood culture bottles 10 that are already in stock so that when a phlebotomist gathers the implements needed for taking a blood culture, the initial discard container 22 is brought along with the blood culture bottle(s) 10. Advantageously, if a separate connector is sized for connecting to both the blood culture bottle 10 and the initial discard container 22, such as the connectors 46, 54 of FIGS. 8-9, the connectors may be sold separately and reused with new initial discard containers 22 after the used initial discard container 22, filled with blood, is discarded. Additionally, some connectors, such as the connector 46 of FIG. 8, may include sufficient space for applying identifying labels. Furthermore, one or more of the above-described connectors may provide a space for storing extra labels to be applied to the bottles 10.

Using the connectors described above, or other suitable connectors, the present disclosure provides a method of enhancing compliance with the DVM, thereby reducing blood culture contaminations and false positives in blood tests. Accordingly, an exemplary method may include attaching an initial discard container 22 to a blood culture bottle 10 so that a phlebotomist may easily handle all the implements necessary for obtaining a blood culture from a patient. Alternatively, the method may include forming the initial discard container 22 extending from and/or connected to the blood culture bottle 10. In yet another non-limiting example, the method may include providing a blood culture kit that includes the initial discard container 22 and a connector configured to connect the initial discard container to the blood culture bottle 10.

Figure 11:
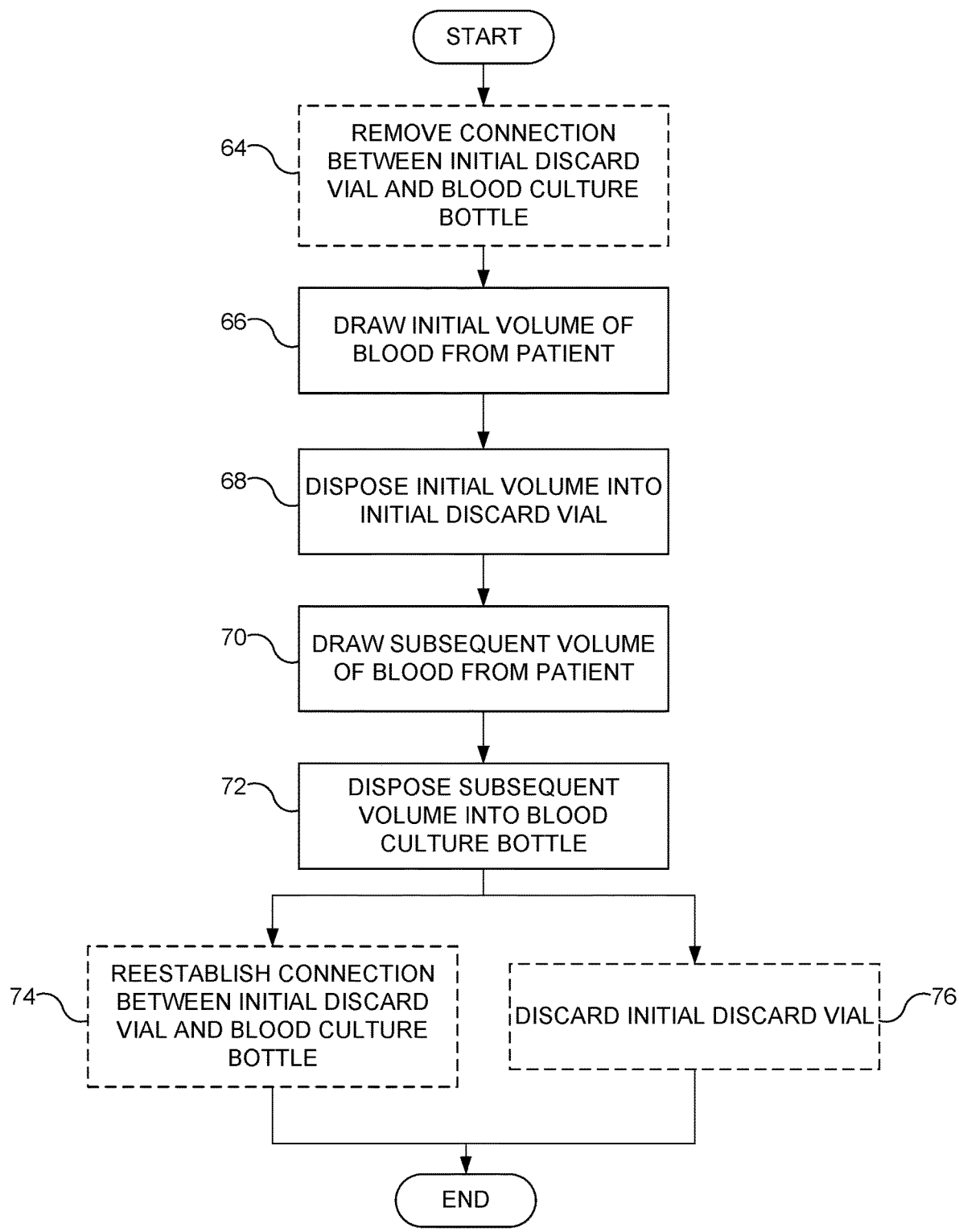
FIG. 11 shows a method for reducing blood culture contamination during a blood draw.

FIG. 11 illustrates a method for reducing blood culture contamination during a blood draw using the initial discard container and any one of the above-described connectors. For example, the method of FIG. 11 may be used with a kit including a set of blood culture bottles 10, an initial discard container 22, and a connector (such as any one of the connectors described with respect to FIGS. 1-10). The method includes a first optional step 64 of removing a connection between the initial discard container 22 and the blood culture bottle(s) 10. Next, at step 66, an initial amount of blood is drawn from a patient, such as between about 5 ml and about 10 ml. At step 68, the initial amount of blood is placed or disposed in the initial discard container 22. Additional blood to be tested is then subsequently drawn at step 70, and placed or disposed in the blood culture bottle 10 at step 72. The method then includes an optional step 74 of reestablishing the connection between the initial discard container 22 and the blood culture bottle 10 or an optional step 76 of discarding the initial discard container 22.

According to the above-described apparatus and methods, the initial discard container 22 specifically for containing the initial volume of blood drawn from a patient in the DVM may advantageously be included in connection to or packaged with other tools needed for the DVM. Adding the initial discard container 22 for any blood culture preparation enhances usage of the DVM by increasing convenience, decreasing costs, and serving as a physical and visual reminder to follow the steps of the DVM. By enhancing the usage of the DVM, the present disclosure provides ways in which the rate of false positives and blood culture contamination may be reduced.

The present disclosure has described terms of one or more preferred configurations, and it should be appreciated that many equivalents, alternatives, variations, and modifications, aside from those expressly stated, are possible and within the scope of the present disclosure.

The invention claimed is:

1. An initial discard container for use with a blood culture bottle and for enhancing compliance with the discard volume method for drawing blood from a patient, the blood culture bottle having an exterior surface, the initial discard container comprising:
    a body with an opening and an inner volume sized to contain an initial amount of blood drawn from the patient, the inner volume being smaller than an inner volume of the blood culture bottle;
    a cap configured to cover the opening and seal the inner volume; and
    a connector integral with and extending from a bottom of the body, the connector configured to couple the initial discard container to the blood culture bottle, the connector including a flexible attachment mechanism configured to clip around the exterior surface of the blood culture bottle by a compression fit, the connector including a support member extending from the body and configured to separately contact the exterior surface of the blood culture bottle to stabilize the connector against the blood culture bottle.

2. The container of claim 1, wherein the inner volume of the initial discard container is between 5 ml and 10 ml.

3. The container of claim 1, wherein the connector includes an intermediate portion that separates the flexible attachment mechanism from the body.

4. The container of claim 1, wherein the connector includes a second flexible attachment mechanism configured to clip around an exterior surface of a second blood culture bottle by a compression fit.

5. The container of claim 1, wherein the flexible attachment mechanism is configured to releasably attach to one of a neck and a base of the blood culture bottle.

6. The container of claim 1, wherein the flexible attachment mechanism is sized to fit around between half of and an entire circumference of the blood culture bottle.

7. A system for reducing blood culture contamination when drawing blood from a patient, the system comprising:
    an initial discard container;
    a first blood culture bottle larger than the initial discard container and configured to contain subsequent blood drawn from the patient to be tested, the first blood culture bottle having a first exterior surface;

a second blood culture bottle larger than the initial discard container and configured to contain subsequent blood drawn from the patient to be tested, the second blood culture bottle having a second exterior surface; and the initial discard container including:
- a body with an opening and an inner volume sized to contain an initial amount of blood drawn from the patient, and
- a connector integral with and extending from a bottom of the body, the connector including a first flexible attachment mechanism and a second flexible attachment mechanism extending from the bottom of the body via a first intermediate portion and a second intermediate portion, respectively, the first flexible attachment mechanism configured to clip around the first exterior surface of the first blood culture bottle by a compression fit, and the second flexible attachment mechanism configured to clip around the second exterior surface of the second blood culture bottle by a compression fit, the connector further including a support bar connecting the first intermediate portion to the second intermediate portion.

8. The system of claim 7, wherein each of the first blood culture bottle and the second blood culture bottle includes a neck and a base, wherein the connector is configured to couple the initial discard container to the neck of the first blood culture bottle and the second blood culture bottle.

9. The system of claim 7, wherein the support bar is curved upwardly, the support bar being configured to provide a finger rest for a subject.

* * * * *